United States Patent [19]

Cope

[11] 4,405,314
[45] Sep. 20, 1983

[54] APPARATUS AND METHOD FOR CATHETERIZATION PERMITTING USE OF A SMALLER GAGE NEEDLE

[75] Inventor: Constantin Cope, Elkins Park, Pa.

[73] Assignee: Cook Incorporated, Bloomington, Ind.

[21] Appl. No.: 369,598

[22] Filed: Apr. 19, 1982

[51] Int. Cl.³ .................... A61B 17/00; A61M 5/00
[52] U.S. Cl. .................................. 604/51; 604/104; 604/164; 604/170; 604/264; 604/281
[58] Field of Search .................. 604/51, 52, 53, 93, 604/95, 104, 158, 164, 170, 264, 280, 281; 128/772, 658, 7

[56] References Cited

U.S. PATENT DOCUMENTS

| | | | |
|---|---|---|---|
| 1,968,997 | 8/1934 | Drucker | 604/164 X |
| 2,118,631 | 5/1938 | Wappler | 604/170 |
| 2,856,934 | 10/1958 | Petillo | 604/170 |
| 3,539,034 | 11/1970 | Tafeen | 604/164 |
| 3,640,281 | 2/1972 | Robertson | 604/264 X |
| 3,749,134 | 7/1973 | Slingluff et al. | 604/280 X |
| 3,752,158 | 8/1973 | Kariher | 604/133 |
| 3,804,097 | 4/1974 | Rudie | 604/51 X |
| 3,860,006 | 1/1975 | Patel | 604/164 |
| 3,920,023 | 11/1975 | Dye et al. | 604/51 |
| 3,924,633 | 12/1975 | Cook et al. | 604/104 |
| 4,212,304 | 7/1980 | Finney | 604/170 |
| 4,230,123 | 10/1980 | Hawkins, Jr. | 604/51 |
| 4,306,562 | 12/1981 | Osborne | 604/164 X |

Primary Examiner—Richard J. Apley
Assistant Examiner—Michelle Nicole Lester
Attorney, Agent, or Firm—Woodard, Weikart, Emhardt & Naughton

[57] ABSTRACT

An introducing catheter for use with a pair of different diameter wire guides, the larger of which is a J-type wire guide, is provided in order to enlarge a tract to facilitate the passage of a drainage catheter through the tract. The introducing catheter includes an inwardly curved portion which lies between the distal and proximal ends of the catheter with the curved portion being located nearer to the distal end. The catheter also has a flexible tapered tip at its distal end and a lumen which decreases in area towards the distal end. The catheter further has a side port which is distally positioned from the curved portion and on the inward side of the curved portion so that when a J-type wire guide is advanced within the catheter from the proximal end, the wire guide will automatically emerge through the side port. The side port has an oval or elliptical shape with its major axis along the length of the tube. The catheter lumen has a diameter at the distal end which is substantially smaller than the minor axis diameter of the side port so that a wire guide having a substantially smaller external diameter than that of the J-type wire guide may be used as a guide for the catheter distal end. The introducing catheter is radiopaque, so that its position within a body can be monitored. The introducing catheter has a base portion at the proximal end for grasping and manipulating the catheter during a catheterization.

11 Claims, 9 Drawing Figures

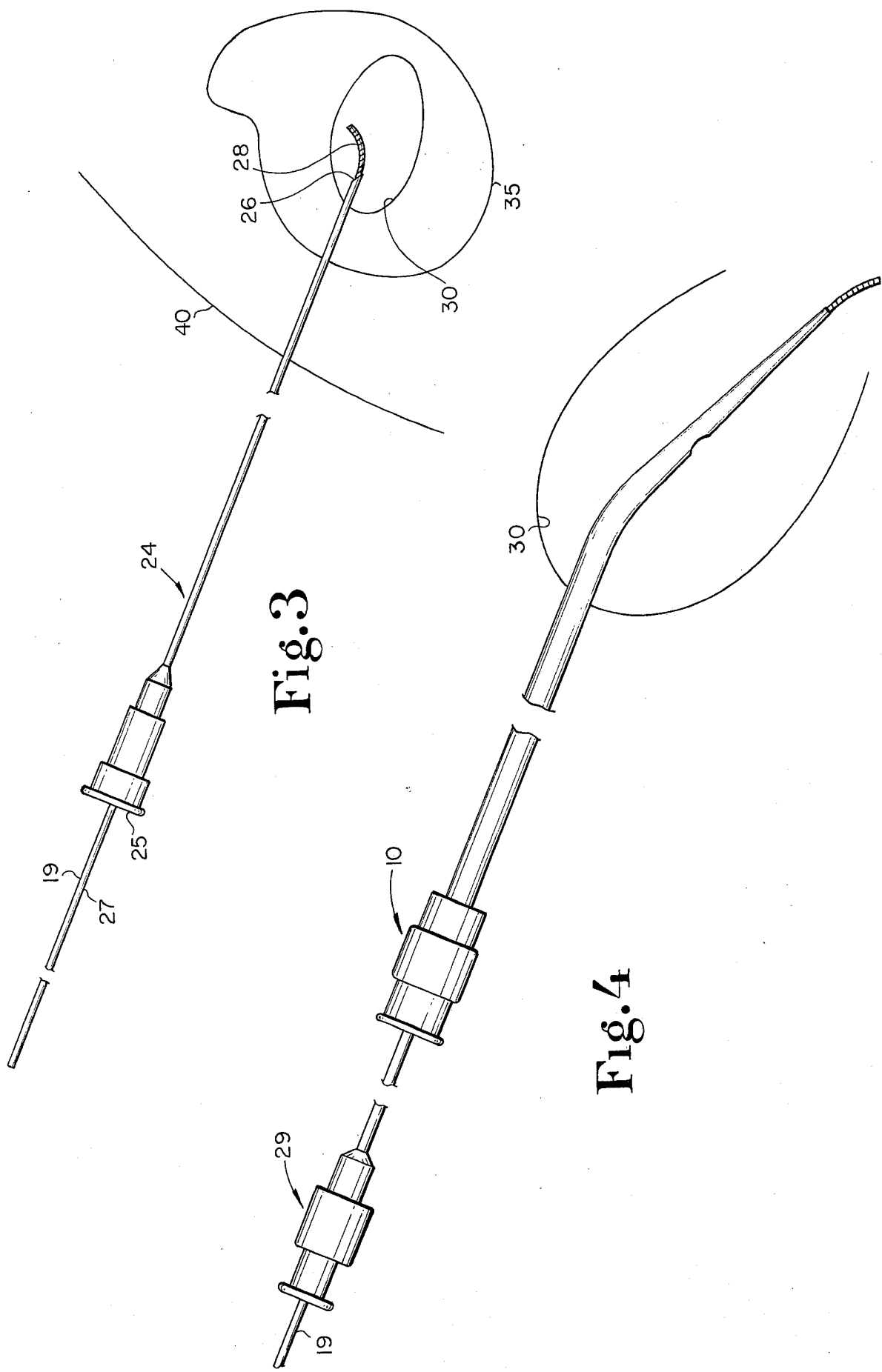

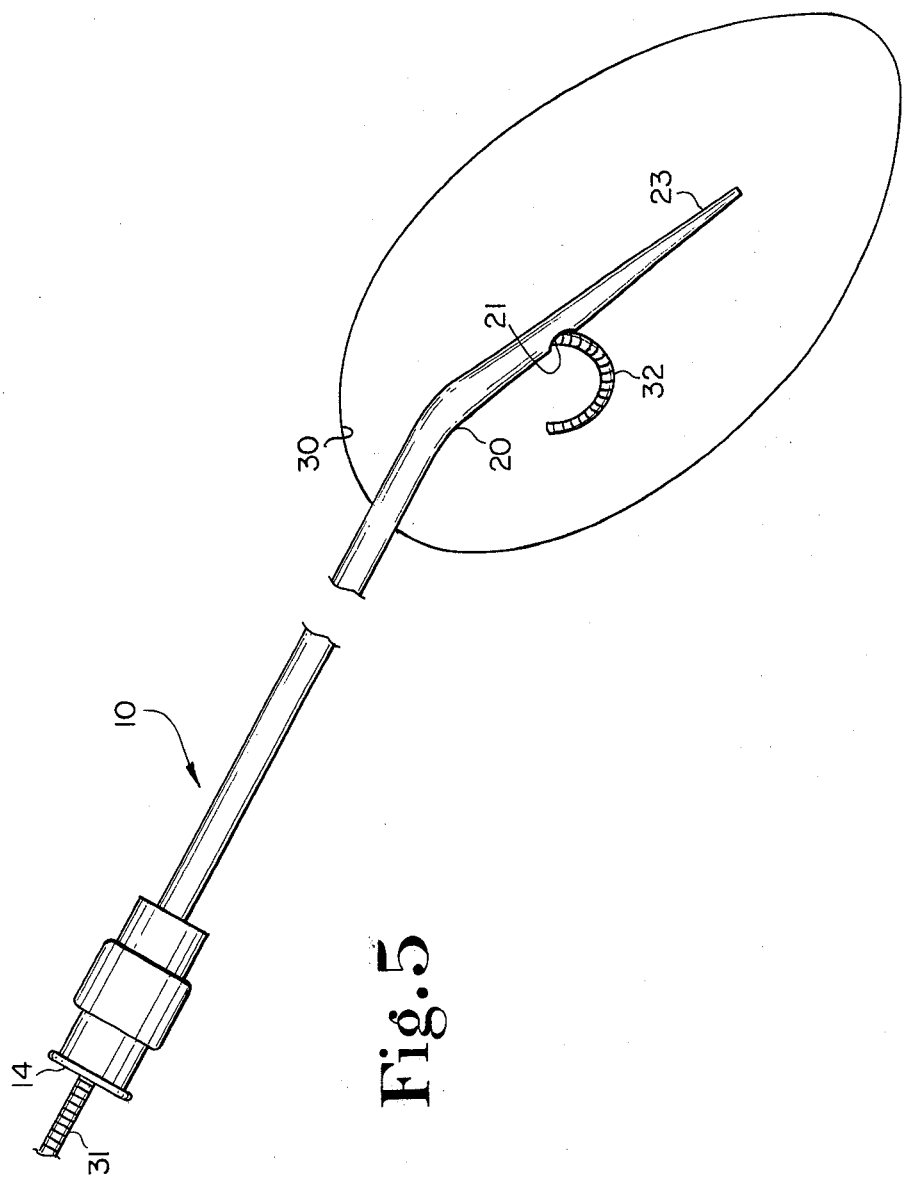

APPARATUS AND METHOD FOR CATHETERIZATION PERMITTING USE OF A SMALLER GAGE NEEDLE

BACKGROUND OF THE INVENTION

1. Field of the Invention

The invention relates generally to the field of catheters and, more particularly, to the catheterization of organs such as the renal pelvis or the like.

2. Description of the Prior Art

Present procedures for percutaneous introduction of large bore drainage catheters in order to drain blocked cavities or ducts such as the renal pelvis and the biliary duct are, at best, somewhat hazardous. For instance, one widely practiced method for obtaining long term drainage of an obstructed upper urinary tract is to perform a percutaneous nephrostomy which involves catheterization of the renal pelvis. In order to install the drainage catheter, an initial percutaneous puncture into the renal pelvis may be made with a hollow 18 gauge (1.3 mm) needle. Then, a guide wire is advanced inside the needle until properly positioned whereupon the needle is removed over the guide wire. Appropriately sized fascial dilators are then advanced over the guide wire to enlarge the tract so as to facilitate the subsequent passage of the drainage catheter over the guide wire. A similar technique is used to install a drainage catheter into the biliary duct for transhepatic antigrade biliary drainage.

The initial puncture made in attempting to enter the renal pelvis of the kidney or the biliary tract is seldom a direct hit. For this reason, several punctures are commonly required in order to properly position the needle. The resulting damage to the kidney or biliary duct can be very traumatic for the patient, especially since the kidney or biliary duct is usually already traumatized by disease. Thus, physicians would obviously prefer using a smaller gauge needle in making this initial puncture, so as to minimize the damage and resulting trauma caused by multiple punctures.

Suprapublic catheterization methods and devices which involve percutaneous entry by a puncturing device are disclosed in U.S. Pat. No. 3,752,158 to Kariher; U.S. Pat. No. 3,860,006 to Patel; and U.S. Pat. No. 3,924,633 to Cook et al. U.S. Pat. No. 3,640,281 to Robertson and U.S. Pat. No. 3,920,023 to Dye et al. disclose methods for draining the urinary bladder by inserting the catheter transurethrally into the bladder.

Other catheterization devices which may have some general relevance are disclosed in U.S. Pat. No. 2,118,631 to Wappler; U.S. Pat. No. 2,856,934 to Petillo; U.S. Pat. No. 3,804,097 to Rudie; and U.S. Pat. No. 4,212,304 to Finney. None of the above patents, however, discloses a method or apparatus which minimizes the damage and trauma caused by catheterization of cavities or ducts which because of their small size or difficult to reach location commonly require multiple punctures to properly position the catheter.

Accordingly, it is an object of the present invention to provide an apparatus and method which minimizes the damage and trauma caused by catheterization procedures which are commonly characterized by multiple punctures in attempting to properly position the puncturing device.

It is a further object of the present invention to provide an apparatus and method for catheterization which permits the use of a smaller gauge hollow needle than would otherwise be necessary using present devices or techniques.

It is a yet further object of the present invention to provide a method for catheterization using a smaller gauge hollow needle which method is relatively simple to follow and requires relatively inexpensive additional equipment.

These and other objects and advantages of the present invention will become more apparent in the following figures and detailed description.

SUMMARY OF THE INVENTION

One embodiment of this invention might include an introducing catheter for use with a plurality of different diameter wire guides, the larger of which is a J-type wire guide, in order to enlarge a tract and facilitate the passage of a drainage catheter through said tract. There is provided a tube having proximal and distal open ends and curved inwardly for a portion of its length between the distal and proximal ends. The tube also has a tapered tip at its distal end and a lumen which decreases in size towards the distal end. The tube also has a side port which is distally positioned from the curved portion and is located along the inward side of the curved portion so that when a J-type wire guide is advanced within the tube from the proximal end, the wire guide will automatically emerge through the side port. It should be understood that the "J-type" wire guide has a tip which is spring biased into a J-shape but is capable of being straightened by overcoming the bias. The lumen of the tube has a diameter at the distal end of the tube which is substantially smaller than the diameter of the side port so that a wire guide having a substantially smaller external diameter than that of the J-type wire guide may be used as a guide means for the distal end of the catheter.

BRIEF DESCRIPTION OF THE DRAWINGS

FIGS. 2-7 are elevational views, partially in section, showing successive steps in practicing the method of the subject invention.

DESCRIPTION OF THE PREFERRED EMBODIMENT

Figure 1:
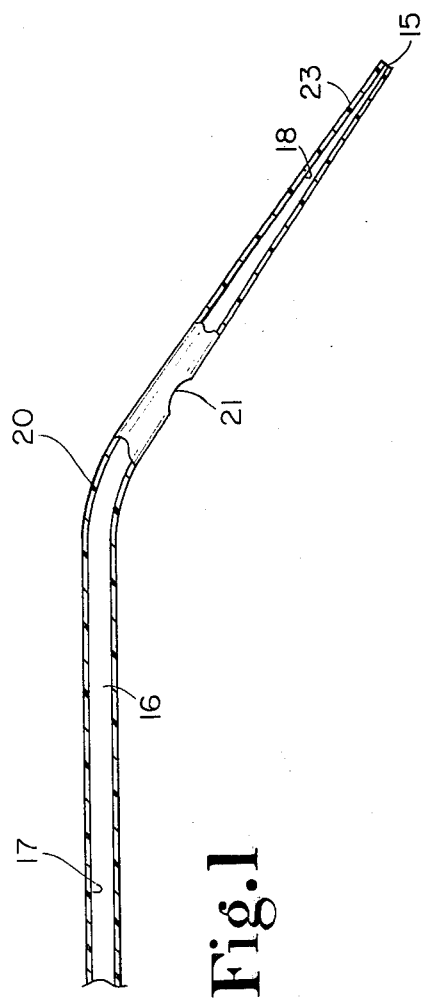
FIG. 1 is an elevation view partially in section of the introducing catheter of the subject invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, introducing catheter 10 includes a 6.3 French sized tubular shaped member 11 and base portion 12 which is press fitted for fixed attachment to tubular member 11. Base portion 12 facilitates the grasping and manipulating of introducing catheter 10 in practicing the method of the subject invention. Introducing catheter 10 is open at proximal end 14 and distal end 15. Further, introducing catheter 10 has a lumen or hollow interior 16 which is relatively large in the area 17, but which tapers to a very small internal diameter at the area 18 which at the distal end 15 is only slightly larger than the external diameter of wire guide 19 shown in FIG. 3. The catheter 10 is also externally tapered from the 6.3 French size down to the distal end 15. The axial length of this taper in the preferred embodiment is approximately 1.5 cm and the thickness of the material is such at the distal end 15 that a relatively sharp or thin edge is presented at distal end 15. Introducing catheter 10 is inwardly curved along portion 20 of its length and has a total length in the preferred embodiment of approximately 22 cm. Side port 21 is located slightly distal to curved portion 20 and along the inner side of the curved portion. Side port 21 is sized to permit passage therethrough of J-type wire guide 31 which is shown in FIG. 5.

Figure 1A:
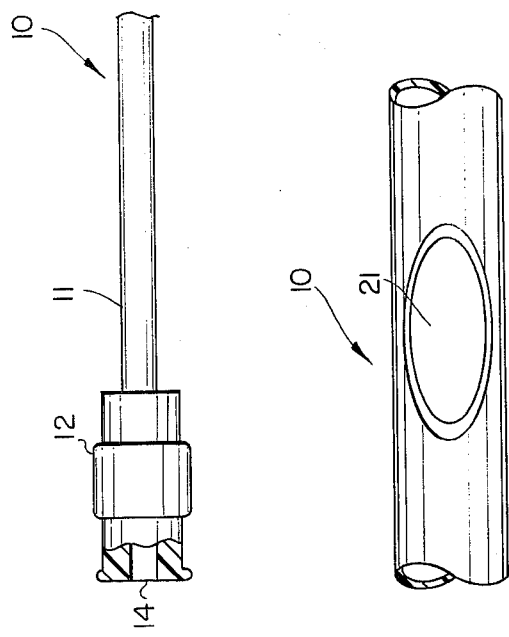
FIG. 1A is an enlarged fragmentary detail view of the introducing catheter showing the configuration of a side port forming a part thereof.

Curved portion 20 and side port 21 are located sufficiently near distal end 15 so that side port 21 and distal end 15 can both be within the renal pelvis 30 when introducing catheter 10 is introduced into the renal pelvis, as will be more fully discussed hereafter. Preferably, side port 21 has an oval or elliptical shape (FIG. 1A) with its major axis parallel to the longitudinal axis of introducing catheter 10. With the side port 21 thus formed and positioned, J-type wire guide 31 will automatically emerge through side port 21 when advanced from proximal end 14 as will also be more fully described hereafter. Introducing catheter 10 is formed of flexible material such as plastic which is capable of being straightened by the introduction into the catheter of a stiffening cannula. Preferably, introducing catheter 10 is formed of a polyethylene material and is radiopaque, so that positioning of the introducing catheter can be monitored on a fluoroscope.

Figure 2:
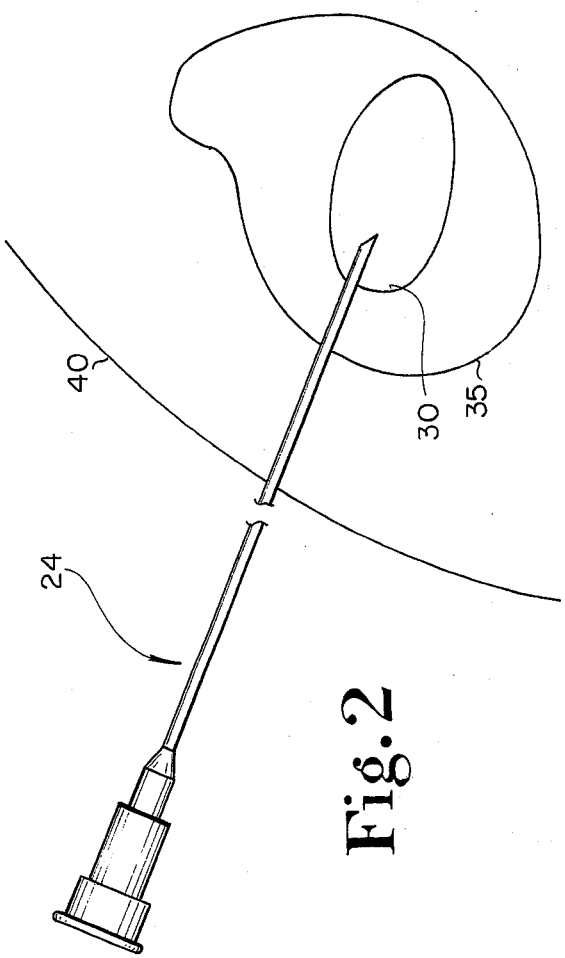

Referring now to FIG. 2, in order to perform a percutaneous nephrostomy a conventional hollow thin wall needle 24 is inserted percutaneously into the body 40 in order to make an initial puncture into the renal pelvis 30 of the kidney 35. It is to be understood that the instruments other than introducing catheter 10 are well known in the art and are manufactured in many standard sizes according to the specific requirements of different procedures. It is also to be understood that while the previous known technique for a percutaneous nephrostomy would require an 18 gage (1.3 mm) needle, practicing the method of the subject invention requires only a 21 gage (0.46 mm) needle in the present preferred embodiment. Preferably, needle 24 is 15 cm in length and is made of stainless steel. As is common in similarly performed nephrostomy procedures it is to be understood that several attempts may be required to obtain a successful nephrostomy puncture. Thus, since needle 24 has a much smaller diameter than the needle previously required for this step, the damage to kidney 35 is minimized.

Referring now to FIG. 3, once needle 24 is successfully positioned with the tip in the renal pelvis, wire guide 19 is inserted in the needle at proximal end 25 and passed completely therethrough until it projects slightly from distal end 26 of the needle. Wire guide 19, which is of a type well known in the art, has a stiff wire shaft portion 27 and a flexible gently curved spring tip portion 28. Portions 27 and 28 are formed and connected in a well known manner. In the preferred embodiment, wire guide 19 is approximately 60 cm long and has an external diameter of approximately 0.46 mm. The needle 24 then is withdrawn from the body over wire guide 19 while the wire guide is still in place within the renal pelvis 30.

Figure 4A:
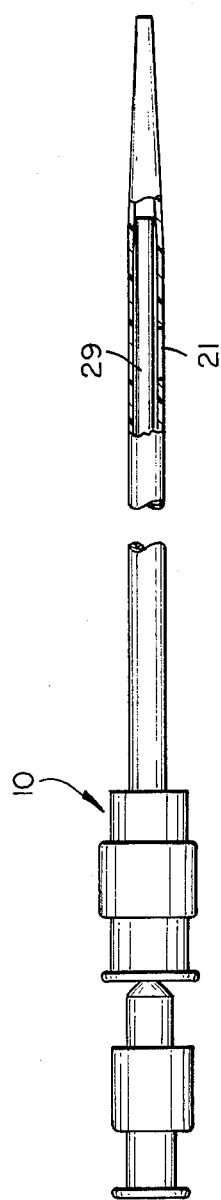
FIG. 4A is an elevational view similar to FIG. 4 but partially in section and showing the relationship of the introducing catheter and a stiffening cannula fully inserted therein.
Figure 6:
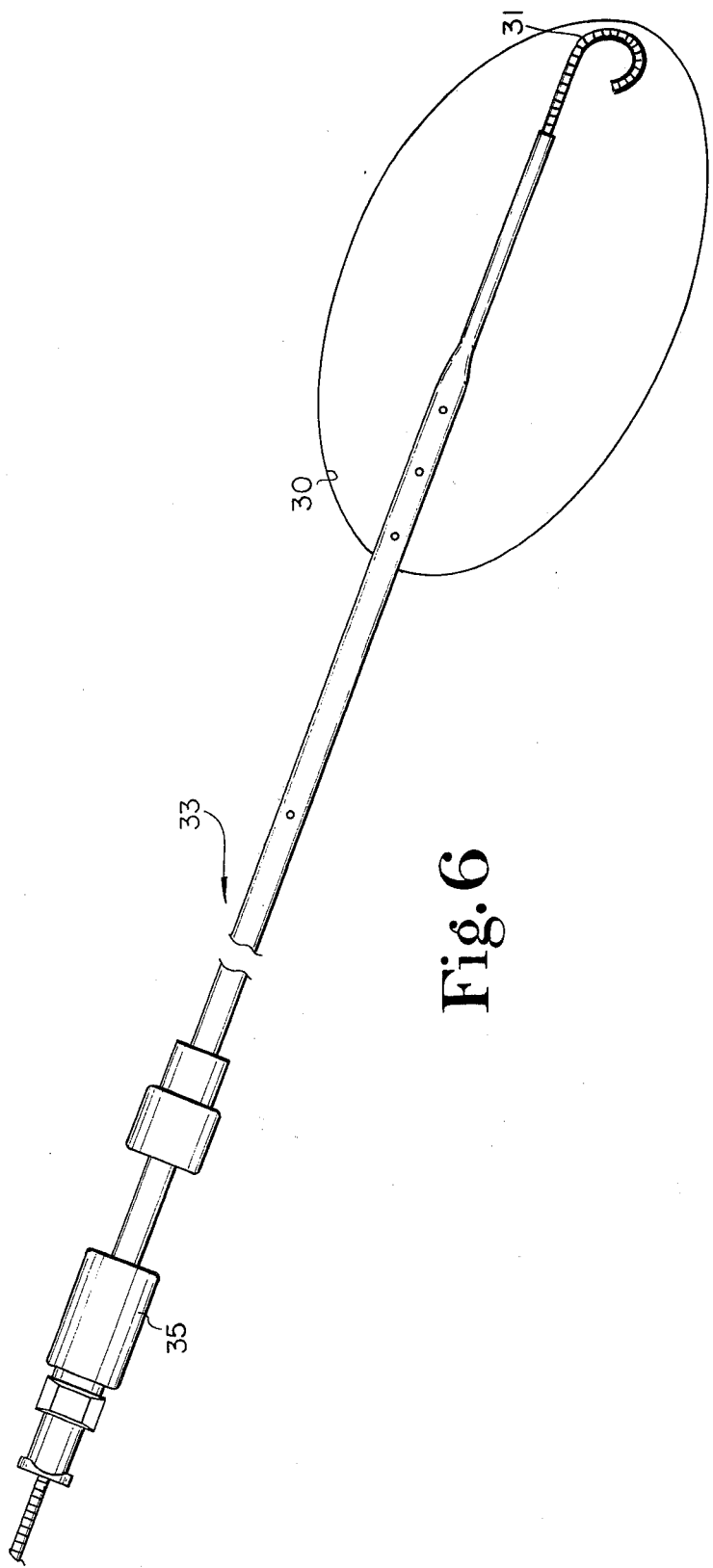

Referring now to FIGS. 4 and 4A, stiffener cannula 29 is fully inserted into introducing catheter 10 as in FIG. 4A in order to reinforce and straighten the otherwise relatively flexible introducing catheter 10 so that it may be more easily introduced into the body as hereinafter described. Cannulas such as stiffening cannula 29 shown in FIG. 3 are well known in the art. Stiffening cannula 29 is preferably of 20 gauge (0.89 mm O.D.) formed of stainless steel and approximately 20 cm in length. The cannula 29 is thin walled having 0.64 mm I.D. so as to slidably fit the O.D. of the wire guide 19. The catheter 10 and cannula 29 are then advanced over wire guide 19 under fluoroscopic monitoring with a rotary motion through the tissues to a depth of 5 to 7 cm. While the patient holds his breath, introducing catheter 10 is then advanced over the cannula 29 until 3 to 5 cm of the thicker non-tapered portion of catheter 10 lies within the renal pelvis 30. Wire guide 19 should not kink as long as the operator constantly rotates introducing catheter 10 as it is advanced. Wire guide 19 and cannula 29 are then removed while firmly holding introducing catheter 10 in its place relative to renal pelvis 30, and aspiration and irrigation are accomplished. Next, as shown in FIG. 5, J-type wire guide 31, which has a well known construction, is threaded through the proximal end 14 of the introducing catheter. J-type wire guide 31, is composed of a helically wound strip of spring metal, such as stainless steel. J-type wire guide 31 preferably has an external diameter of approximately 0.97 mm and has a total length of approximately 100 cm. J-type wire guide 31 also has a flexible J-curved tip 32 at its distal end and maintains the J-shape by a spring bias. J-type wire guide 31 is available from Cook, Inc. of Bloomington, Ind., or from Vance Products, Inc., of Spencer, Ind., under part no. 07006.

In order to put the J-type wire guide 31 into the introducing catheter, the curved tip 27 is straightened. This can be done by pulling the turns of the J-type wire guide apart towards the proximal end thereof, or it can be done by merely taking the fingers and straightening the J-shape. However, it should be understood that the flexible curved tip 32 assumes the J configuration in a spring biased fashion, but against the urging of the spring can be straightened out into a straight line configuration. The flexible curved tip 32 however, does tend to attempt to return to the J configuration illustrated in FIG. 5. Thus, as the J-type wire guide 31 is moved down the inside of the introducing catheter 10, the flexible curved tip 32 is attempting to assume the illustrated J shape. It of course cannot do so, because the inside of the introducing catheter guides it until it reaches the curved portion 20 at which point the J configuration orients itself so that the J curved tip 32 is in the same direction as the curved portion 20. Thus, as the J tip moves down toward and to the side port 21 it will be so oriented, that as soon as it gets to side port 21 the J tip automatically passes through the side port.

Figure 7:
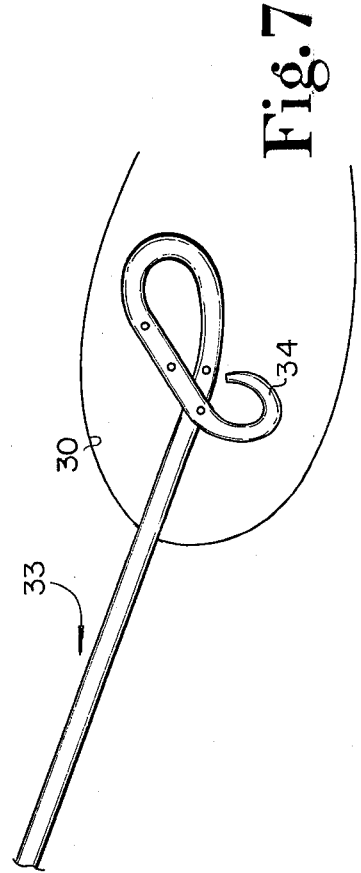

It should be understood that the tip 23 of the introducing catheter is sufficiently projected into the renal pelvis 30 so that the location of side port 21 is within the area of the renal pelvis that is to be drained. The next step is to withdraw the catheter 10 from the body by removing it over the J-type wire guide 31. Of course as it is withdrawn it will move alongside the wire guide 31. J-type wire guide 31 is then used for inserting a loop nephrostomy drainage catheter 33. Loop drainage catheter 33 is of a type similar to that disclosed in U.S. Pat. No. 3,924,633 to Cook et al. and is avilable through Cook, Inc. of Bloomington, Ind., under catalog No. NCL-1. Catheter 33 has a drawstring (not shown) attached at distal end 34 which when drawn from proximal end 35 causes distal end 34 to form into a tight self-retaining loop such as shown in FIG. 7, thus anchoring drainage catheter 33 firmly inside renal pelvis 30. One method of anchoring is described in U.S. Pat. No. 3,924,663 to Cook et al. Drainage catheter 33 has a 10 French size at its largest diameter and is 25 cm in length.

While the foregoing description applies to a percutaneous nephrostomy, it is to be understood that the introducing catheter and catheterization method of the subject invention can be used for catheterization of other cavities or ducts. One such similar application would involve the installation of a drainage catheter into the biliary duct for transhepatic antigrade biliary drainage. Of course, it is to be understood that the size and lengths of the catheters, wire guides, and cannula as disclosed herein are suited for a percutaneous nephrostomy, and may therefore vary when used in conjunction with other medical procedures.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. An introducing catheter for use with a plurality of different diameter wire guides, the larger of which is a J-type wire guide, in order to enlarge a tract and facilitate the passage of a larger diameter catheter through said tract, said introducing catheter comprising:

a tube having proximal and distal open ends, said tube having an inwardly curved portion between said ends, said tube having a tapered tip at said distal end, said tube also having a lumen, the size of said lumen decreasing towards said distal end, said tube further having a side port which is distally positioned from said curved portion and along the inward side of said curved portion so that when a J-type wire guide is advanced within said tube from said proximal end the guide will automatically emerge through said side port, said lumen having a diameter at said distal end which is substantially smaller than the diameter of said side port.

2. The apparatus of claim 1 wherein said inwardly curved portion is located closer to said distal end than to said proximal end.

3. The apparatus of claim 2 wherein said side tube is radiopaque and said port is elliptically shaped and has its major axis along the length of said tube, said lumen having a diameter at said distal end which is substantially smaller than the minor axis diameter of said port.

4. The apparatus of claim 3 and further comprising: a base portion fixed to said tube at said proximal end for grasping and manipulating said introducing catheter during a catheterization.

5. A kit used for performing a percutaneous nephrostomy, comprising:

a hollow thin wall needle, said needle having a lumen therethrough;

a first wire guide, said first wire guide having a diameter sized to permit the first wire guide to be received within the lumen of said needle;

an introducing catheter, said introducing catheter including a tube having proximal and distal open ends, said tube having an inwardly curved portion between said ends, said tube having a tapered tip at said distal end, said tube also having a lumen, the size of said lumen decreasing towards said distal end, said tube further having a side port which is distally positioned from said curved portion and along the inward side of said curved portion, said lumen having a diameter at said distal end which is sufficiently large to receive therethrough said first wire guide;

a stiffening cannula, said stiffening cannula having proximal and distal open ends and a lumen therethrough, said cannula sized to be received within said introducing catheter, said cannula having an outer diameter which is larger than the lumen of said introducing catheter at the distal end, the lumen of said cannula sized to receive the first guide wire therethrough;

a second wire guide, said second wire guide having a flexible J-tip, said second wire guide having a diameter which is substantially larger than the diameter of said first wire guide and the lumen of said introducing catheter at the distal end, said second wire guide sized to be received through the proximal end and the side port of said introducing catheter;

a drainage catheter, said drainage catheter having a lumen therethrough sized so that said second wire guide may be received through said drainage catheter.

6. The kit of claim 5, wherein said needle is a 21 gauge needle, said first wire guide has a diameter of 0.46 mm, said second wire guide has a diameter of 0.97 mm, and said stiffening cannula is 21 gauge having an inner diameter of 0.46 mm.

7. A method for inserting a catheter into a body cavity, comprising the steps of:

(1) percutaneously inserting a needle having a lumen into a desired position projecting into the body cavity;

(2) inserting a first wire guide through the lumen of the needle so that it projects from the distal end of the needle into the body cavity;

(3) withdrawing the needle from the first wire guide while maintaining the wire guide within the body cavity;

(4) advancing an introducing catheter over the first wire guide to the desired position within the body cavity while maintaining the position of the first wire guide relative to the body cavity;

(5) removing the first wire guide from the introducing catheter while maintaining the introducing catheter in its position relative to the body cavity.

(6) inserting into said introducing catheter a J-type wire guide having a substantially larger diameter than the internal diameter of said introducing catheter at its distal end;

(7) causing said J-type wire guide to automatically emerge through a side port in said introducing catheter by causing said wire guide to move around a curve to said introducing catheter and by positioning the side port on the inside of said curve and toward the distal end of the introducing catheter;

(8) removing said introducing catheter from said J-type wire guide while maintaining the position of said J-type wire guide relative to said body; and (9) advancing a drainage catheter over said J-type wire guide to a desired position within the body cavity while maintaining the position of said J-type wire guide relative to said body.

8. The method of claim 7 including the following additional steps:

inserting a stiffening cannula into the introducing catheter prior to advancing it over the first wire guide and wherein step 4 includes the following substeps:

(a) advancing the cannula with the introducing catheter received thereover, over the first wire guide to a desired position with the distal end of the cannula in said body cavity while maintaining the position of the first wire guide relative to the body cavity;

(b) advancing the introducing catheter over the cannula to the desired position within the body cavity while continually rotating the introducing catheter around the axis of the cannula;

and step 5 additionally includes removing the cannula and the first guide from the introducing catheter while maintaining the introducing catheter in its position relative to the body cavity.

9. The method of claim 8, wherein the catheters, needle, wire guides and cannula all are radiopaque and the positioning of each element relative to the body is accomplished by X-ray monitoring on a fluoroscope.

10. An introducing catheter combination comprising:

(a) a tube formed of resilient material and having an inwardly curved portion between proximal and distal open ends, said tube having a tapered tip at said distal end, said tube also having a lumen the size of which decreases towards said distal end, said tube further having a side port which is distally located relative to said curved portion and along the inward side of said curved portion, said lumen having a diameter at said distal end which is substantially smaller than said side port;

(b) a stiffening cannula received within said tube and extending into said inwardly curved portion to straighten said curved portion and stiffen said tube, said cannula being removable from said tube to permit said tube to resume its inwardly curved shape.

11. The introducing catheter combination of claim 10 and further comprising:

(c) a wire guide received within said tube and cannula and having an external size approximately the same size as said distal end.

* * * * *

UNITED STATES PATENT AND TRADEMARK OFFICE
CERTIFICATE OF CORRECTION

PATENT NO. : 4,405,314
DATED : September 20, 1983
INVENTOR(S) : Constantin Cope

It is certified that error appears in the above-identified patent and that said Letters Patent is hereby corrected as shown below:

In Column 7, line 29, please insert the word "wire" after "and the first" but before the words "guide from the introducing catheter..."

Signed and Sealed this

Twenty-second Day of November 1983

[SEAL]

Attest:

GERALD J. MOSSINGHOFF

Attesting Officer

Commissioner of Patents and Trademarks